United States Patent [19]

Teraji et al.

[11] Patent Number: 4,618,610
[45] Date of Patent: Oct. 21, 1986

[54] TRIAZINE DERIVATIVES, AND PHARMACEUTICAL COMPOSITIONS COMPRISING THE SAME

[75] Inventors: Tsutomu Teraji, Osaka; Youichi Shiokawa, Ibaraki; Kazuo Okumura, Sakai; Yoshinari Sato, Takaishi, all of Japan

[73] Assignee: Fujisawa Pharmaceutical Co., Ltd., Osaka, Japan

[21] Appl. No.: 603,173

[22] Filed: Apr. 23, 1984

[30] Foreign Application Priority Data

Apr. 22, 1983 [JP] Japan .................................. 58-72013

[51] Int. Cl.⁴ .................... C07D 253/06; A61K 31/53
[52] U.S. Cl. ...................................... 514/242; 544/182
[58] Field of Search .......................... 544/182; 514/242

[56] References Cited

U.S. PATENT DOCUMENTS 4,495,185  1/1985  Brown et al. ........................ 544/182
4,503,054  3/1985  Brown et al. ........................ 544/182

OTHER PUBLICATIONS

Boicheva et al, Chemical Abstract, vol. 91, Abstract No. 107 924k, 1979, p. 578.
Nakayama et al, Chemical Abstract, vol. 95, Abstract No. 97 744t, 1981, pp. 651 & 652.
Daunis et al, Chemical Abstract, vol. 91, Abstract No. 5 206k, 1979, p. 490.
Werber et al, Chemical Abstract, vol. 86, Abstract No. 29 123d, 1976, p. 307.

*Primary Examiner*—John M. Ford
*Attorney, Agent, or Firm*—Oblon, Fisher, Spivak, McClelland & Maier

[57] ABSTRACT

New triazine derivatives represented by the formula:

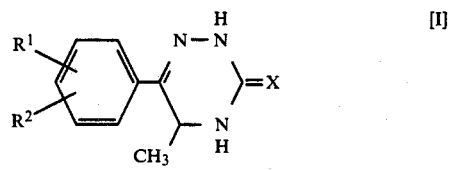

wherein
$R^1$ is hydrogen or halogen;
$R^2$ is a hydroxy, protected hydroxy, amino, cyano, mercapto, lower alkylthio, arylthio, sulfamoyl, lower alkylsulfonylamino, lower alkylureido, arylureido, lower alkyl-thioureido, aryl-thioureido, lower alkenoylamino, lower alkoxycarbonylamino, lower alkoxy(thiocarbonyl)thio, or cyclic or acyclic alkanoylamino in which the cyclic and acyclic alkanoylamino group may have a substituent selected from lower alkoxy, aryl, hydroxyaryl and protected hydroxyaryl; and
X is O or S;

and pharmaceutically acceptable salt thereof, which are useful in the treatment of hypertension, thrombosis and ulcer in human beings and animals.

12 Claims, No Drawings

TRIAZINE DERIVATIVES, AND PHARMACEUTICAL COMPOSITIONS COMPRISING THE SAME

The present invention relates to novel triazine derivatives and pharmaceutically acceptable salts thereof. More particularly, it relates to novel, 6-substituted 1,2,4-triazine and pharmaceutically acceptable salts thereof which have antihypertensive activity, inhibitory activity on platelet aggregation and anti-ulcer activity, to processes for preparation thereof, to pharmaceutical composition comprising the same, and to a method of using the same therapeutically in the treatment of hypertension, thrombosis and ulcer in human beings and animals.

Accordingly, one object of this invention is to provide novel 6-substituted-1,2,4-triazine and pharmaceutically acceptable salts thereof, which are useful as an antihypertensive agent, antithrombotic agent and antiulcer drug.

Another object of this invention is to provide processes for preparation of said triazine derivatives and pharmaceutically acceptable salts thereof.

A further object of this invention is to provide pharmaceutical composition comprising, as an active ingredient, said triazine derivative or its pharmaceutically acceptable salt.

Still further object of this invention is to provide a method of using said triazine derivative or its pharmaceutically acceptable salt in the treatment of hypertension, thrombosis and ulcer in human beings and animals.

With regard to the state of the arts in this field, for example, the European Patent Publication Number 0052442 describes the following 1,2,4-triazin-3(2H)-one compounds.

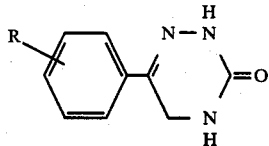

(wherein R is nitro, cyano, amino, methylureido, acetamido, carboxy, lower alkyl, carbamoyl optionally substituted lower alkyl, thiocarbamoyl or morpholinocarbonyl).

It has now been found that certain 6-substituted-1,2,4-triazine compounds which have not been described in any of the references have strong antihypertensive activity, inhibitory activity on platelet aggregation and antiulcer activity.

The object compounds of the present invention include the ones represented by the following formula [I].

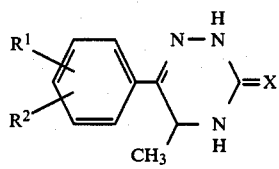

wherein
$R^1$ is hydrogen or halogen;
$R^2$ is a hydroxy, protected hydroxy, amino, cyano, mercapto, lower alkylthio, arylthio, sulfamoyl, lower alkylsulfonylamino, lower alkylureido, arylureido, lower alkyl-thioureido, aryl-thioureido, lower alkenoylamino, lower alkoxycarbonylamino, lower alkoxy(thiocarbonyl)thio, or cyclic or acyclic alkanoylamino in which the cyclic and acyclic alkanoylamino group may have a substituent selected from lower alkoxy, aryl, hydroxyaryl and protected hydroxyaryl; and
X is O or S;
and pharmaceutically acceptable salt thereof.

Suitable illustrations and examples of the above definitions are explained in the following.

The term "lower" is intended to mean a group having 1 to 6 carbon atoms, unless otherwise indicated.

"Halogen" may include chloro, bromo, iodo and fluoro.

Suitable protective group for "protected hydroxy" may include a conventional ones such as substituted or unsubstituted aralkyl (e.g. benzyl, trityl, 4-nitrobenzyl, etc.), substituted or unsubstituted lower alkanoyl (e.g. formyl, acetyl, propionyl, chloroacetyl, etc.), lower alkoxycarbonyl (e.g. methoxycarbonyl, ethoxycarbonyl, t-butoxycarbonyl, etc.), substituted or unsubstituted aralkyloxycarbonyl (e.g. benzyloxycarbonyl, 4-nitrobenzyloxycarbonyl, etc.) and the like.

Suitable "lower alkylthio" may include methylthio, ethylthio, propylthio, isopropylthio, butylthio, pentylthio, hexylthio and the like.

Suitable "arylthio" may include phenylthio, tolylthio, xylylthio, naphthylthio and the like.

Suitable "lower alkylsulfonylamino" may include mesylamino, ethanesulfonylamino, propanesulfonylamino, propane-2-sulfonylamino, butanesulfonylamino, pentanesulfonylamino, hexanesulfonylamino and the like.

Suitable "lower alkylureido" may include 1-methylureido, 3-methylureido, 3-ethylureido, 3-propylureido, 3-isopropylureido, 3-pentylureido, 3-hexylureido and the like.

Suitable "arylureido" may include 1-phenylureido, 3-phenylureido, 3-tolylureido, 3-xylylureido, 3-napthylureido and the like.

Suitable "lower alkyl-thioureido" may include 1-methyl-thioureido, 3-methyl-thioureido, 3-ethyl-thioureido, 3-isopropyl-thioureido, 3-butyl-thioureido, 3-pentylthioureido, 3-hexyl-thioureido and the like.

Suitable "aryl-thioureido" may include 1-phenyl-thioureido, 3-phenyl-thioureido, 3-tolyl-thioureido, 3-xylyl-thioureido, 3-naphthyl-thioureido and the like.

Suitable "lower alkenoylamino" may include acryloylamino, methacryloylamino, crotonoylamino, isocrotonoylamino, 4-pentenoylamino, 5-hexenoylamino and the like.

Suitable "lower alkoxycarbonylamino" may include methxycarbonylamino, isopropoxycarbonylamino, butoxycarbonylamino, pentyloxycarbonylamino, hexyloxycarbonylamino and the like.

Suitable "lower alkoxy(thiocarbonyl)thio" may include methoxy(thiocarbonyl)thio, ethoxy(thiocarbonyl)thio, isopropoxy(thiocarbonyl)thio, butoxy(thiocarbonyl)thio, pentyloxy(thiocarbonyl)thio, hexyloxy(thiocarbonyl)thio, and the like.

Suitable "acyclic alkanoylamino" may include straight or branched alkanoylamino such as formylamino, acetylamino, propionylamino, butyrylamino, isobutyrylamino, valerylamino, pivaloylamino, 2,3-dimethylpentanoylamino, decanoylamino, undecanoylamino, tetradecanoylamino, and the like.

Suitable "cyclic alkanoylamino" may include cyclopropanecarbonylamino, cyclobutanecarbonylamino, cyclohexanecarbonylamino, norbornanecarbonylamino, adamantanecarbonylamino and the like.

The above "cyclic and acyclic alkanoylamino" group may have a substituent selected from lower alkoxy, aryl, hydroxyaryl and protected hydroxyaryl.

Suitable "lower alkoxy" may include methoxy, ethoxy, propoxy, isopropoxy, butoxy, pentyloxy, hexyloxy and the like.

Suitable "aryl" may include phenyl, tolyl, xylyl, mesityl, cumenyl, naphthyl and the like.

Suitable "hydroxyaryl" may include 2-,3-or 4-hydroxyphenyl, 2-hydroxy-4-methylphenyl, 2,6-dimethyl-4-hydroxyphenyl, β-hydroxynaphthyl and the like.

"Protected hydroxyaryl" is the hydroxyaryl substituted with an protective group mentioned above at the hydroxy group.

Suitable "protected hydroxyaryl" may include benzyloxyphenyl, trityloxyphenyl, acetoxyphenyl, 4-benzyloxy-2-methylphenyl and the like.

With regard to the object compound [I], it should be understood that the compounds [I] include all of the possible optical and/or geometrical isomers due to the asymmetric carbon atom(s) and/or double bond(s) in their molecules.

Suitable pharmaceutically acceptable salts of the object compound [I] are conventional non-toxic salts and may include an acid addition salt such as an inorganic acid addition salt (e.g. chloride, bromide, sulfate, phosphate, etc.), an organic acid addition salt (e.g. oxalate, maleate, lactate, tartrate, fumarate, methanesulfonate, benzenesulfonate, toluenesulfonate, etc.) or a salt with an amino acid (e.g. arginine salt, aspartic acid salt, glutamic acid salt, etc.), a salt with a base such as alkali metal salt (e.g. sodium salt, potassium salt, etc.), alkaline earth metal salt (e.g. calcium salt, magnesium salt, etc.) and the like.

The object compounds [I] of the present invention can be prepared by the following processes.

Process 1

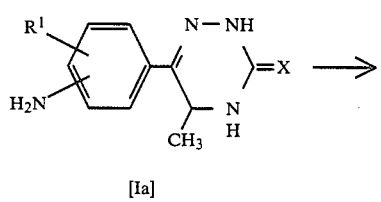

[Ia]

-continued

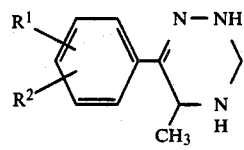
[I]

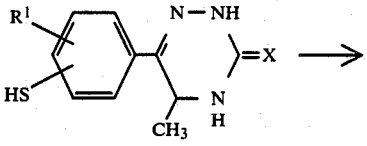
[Iw]

Process 6

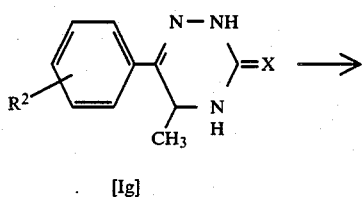
[Ig]

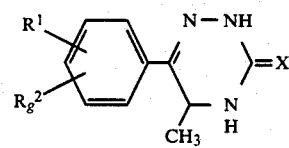
[Im]

Process 10

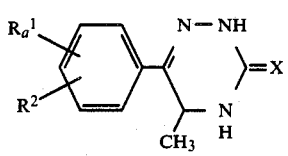
[Ih]

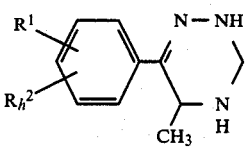
[III]

Process 7

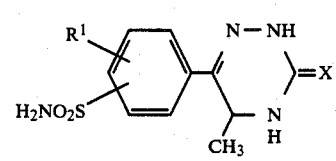
[In]

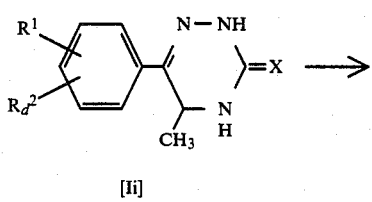
[Ii]

wherein $R^1$, $R^2$ and X are each as defined above;
$R_a{}^1$ is a halogen,
$R_a{}^2$ is a lower alkylsulfonyl, lower alkenoyl, lower alkoxycarbonyl, or cyclic or acyclic alkanoyl in which the cyclic and acyclic alkanoyl group may have a substituent selected from lower alkoxy, aryl, hydroxyaryl and protected hydroxyaryl,
$R_b{}^2$ is a lower alkylureido, arylureido, lower alkylthioureido or aryl-thioureido,
$R_c{}^2$ is a hydroxy, cyano, mercapto, lower alkylthio, arylthio or lower alkoxy(thiocarbonyl)thio,
$R_d{}^2$ is a protected hydroxy or cyclic or acyclic alkanoylamino in which the cyclic and acyclic alkanoylamino group may have a substituent selected from lower alkoxy, aryl, hydroxyaryl and protected hydroxyaryl,
$R_e{}^2$ is a hydroxy, amino or cyclic or acyclic alkanoylamino which is substituted with hydroxyaryl,
$R_f{}^2$ is a lower alkoxy(thiocarbonyl)thio,
$R_g{}^2$ is a lower alkylthio,
$R_h{}^2$ is a halosulfonyl,
$R_i{}^2$ is a hydroxy, protected hydroxy, amino, cyano, mercapto, lower alkylthio, arylthio, sulfamoyl, lower alkylsulfonylamino, lower alkylureido, arylureido, lower alkyl-thioureido, aryl-thioureido, lower alkenoylamino, or cyclic or acyclic alkanoylamino in which the cyclic and acyclic alkanoylamino group may have a substituent selected from lower alkoxy, aryl, hydroxyaryl and protected hydroxyaryl; and
Y is a leaving group.

Process 8

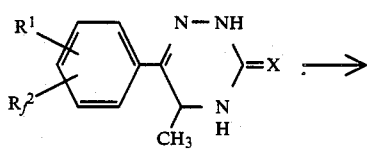
[Ij]

Process 9

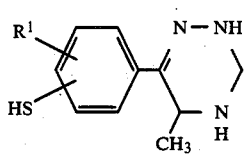
[Ik]

[Iw]

Suitable "halosulfonyl" may include chlorosulfonyl, bromosulfonyl, fluorosulfonyl, iodosulfonyl.

Suitable "leaving group" may include lower alkylthio such as methylthio, ethylthio, propylthio, isopropylthio, butylthio, pentylthio, hexylthio, etc., carboxy(lower)alkylthio such as carboxymethylthio, 2-carboxyethylthio, 3-carboxypropylthio, 2-carboxypropylthio, 4-carboxybutylthio, 5-carboxypentylthio, 6-carboxyhexylthio, etc., hydroxy and the like.

The other definitions of each symbols are exemplified the ones as described hereinbefore.

Preferable reaction conditions of the above processes are explained below but this invention include the modification of the conditions by a person who skilled in the art.

Process 1

The compound [Ib] and its salt can be prepared by acylation of the compound [Ia] or its salt with a corresponding acylating agent having the formula $R_a^2$-Z (wherein $R_a^2$ is as defined above, and Z is a hydroxy or acid residue).

The acylating agent used in this process may include carboxylic acid, sulfonic acid or their reactive derivative.

Suitable "acid residue" is a reactive derivative of carboxylic acid or sulfonic acid.

Suitable "reactive derivative of carboxylic acid or sulfonic acid" may include acid halide such as acid chloride, acid bromide, etc., acid anhydride such as a mixed acid anhydride with an acid (e.g., phosphoric acid, dialkylphosphorous acid, sulfurous acid, sulfuric acid, alkyl carbonate, aliphatic carboxylic acid, aromatic carboxylic acid, etc.), an activated acid amide with a heterocyclic compound (e.g., imidazole, triazole, etc.), an activated ester (e.g., cyanomethyl ester, 2,4-dinitrophenylester, etc.), and the like.

The acylation is preferably carried out in the presence of a base in a solvent under cooling or heating according to a conventional way.

Suitable base may include an amine (e.g., triethylamine, pyridine, N,N-dimethylaniline, etc.), an alkali metal hydroxide (e.g., sodium hydroxide, potassium hydroxide, etc.), an alkali metal carbonate (e.g., sodium carbonate, potassium carbonate, etc.), alkali metal bicarbonate (e.g. sodium bicarbonate, etc.), a salt of an organic acid (e.g., sodium acetate, etc.) and the like. In case that the base is liquid, the base can be used as a solvent.

Suitable solvent may include acetonitrile, chloroform, tetrahydrofuran, ethyl acetate, N,N-dimethylformamide, dimethylsulfoxide or any other solvent or an optional mixture thereof which does not adversely influence the reaction.

Further, when the acylating agent is used in a form of the free acid or its salt in this reaction, the reaction is preferably carried out in the presence of a conventional condensing agent such as a carbodiimide compound, a ketenimine compound, a phosphorus compound and the like.

Process 2

The compound [Ic] and its salt can be prepared by reacting a compound of the formula [Ia] or its salt with isocyanate or isothiocyanate being substituted with alkyl or aryl. This reaction can be conducted in a conventional way and preferably, can be conducted in the presence of a base as exemplified in Process 1 under warming or heating. This reaction is usually conducted in a solvent as exemplified in Process 1 but this reaction can be conducted in a liquid base as a solvent.

Process 3

The compound [Id] and its salt can be prepared by reacting a compound of the formula [Ia] or its salt with organic or inorganic nitrous acid or its salt (e.g. amyl nitrite, isoamyl nitrite, sodium nitrite, etc.) to give a diazonium salt and then by substitution reaction of the diazonium salt.

The preparation of diazonium salt from primary amine can be conducted in a conventional way, for example, by reacting the compound [Ia] or its salt with nitrous acid or its salt in the presence of a mineral acid (e.g. hydrochloric acid, sulfuric acid, etc.) under cooling or ambient temperature. Suitable solvent may include water, acetic acid, chloroform, and the like. The above obtained diazonium compound can be optionally isolated and purified, but it can be used in the second step without isolation.

The substitution reaction of the diazonium salt can be conducted in a conventional way.

For example, in order to produce cyano group for $R_c^2$, the diazonium salt compound is reacted with cyanide compound (e.g. cuprous cyanide, nickel cyanide, etc.). Further, in order to produce mercapto, lower alkylthio, arylthio or lower alkoxy(thiocarbonyl)thio group for $R_c^2$, the diazonium salt compound is reacted with a corresponding thiol compound in the presence of an acid or a base. The substitution reaction can optionally be conducted after neutralization by addition of a base such as an alkali metal carbonate alkali metal bicarbonate as exemplified in Process 1. The reaction temperature is not critical but usually be conducted under cooling to heating. The solvent is the same as exemplified in the initial step.

Process 4

The compound [Ie] and its salt can be prepared by treating a compound [II] or its salt with a base and then reducing the reaction product.

Suitable base to be used in the first step may include alkali metal hydroxide (e.g. sodium hydroxide, potassium hydroxide, etc.), alkaline earth metal hydroxide (e.g. calcium hydroxide, etc.), an alkali metal carbonate (e.g., sodium carbonate, potassium carbonate, etc.), alkali metal bicarbonate (e.g., sodium bicarbonate, etc.), a salt of an organic acid (e.g., sodium acetate, etc.) and the like.

The treatment of the compound [II] or its salt with a base can be preferably conducted in a polar solvent such as alcohol (e.g., methanol, ethanol, propanol, etc.), water, ether (e.g., dimethyl ether, diethyl ether, tetrahydrofuran, dioxane, etc.), aromatic solvent (e.g., benzene, toluene, xylene, etc.).

The reaction product obtained in the initial step is the compound of the following formula [IV] or its salt.

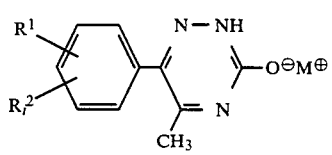

(wherein $R^1$ and $R_f^2$ are each as defined above, and M is an alkali metal or alkaline earth metal ion).

Said compound [IV] and its salt can be optionally isolated and purified, but they can be used in the second step without isolation or purification, also.

The reduction of the compound [IV] can be carried out by a conventional method, for example, by using a reducing agent such as lithium borohydride, sodium borohydride, potassium borohydride, sodium cyanoborohydride or lithium aluminium hydride etc.; by chemical reduction using metal (e.g., zinc, iron, copper, etc.) and acid (e.g., hydrochloric acid, sulfuric acid, etc.), or metal (e.g., sodium, lithium, zinc, etc.) and base (e.g. ammonia, sodium hydroxide, etc.); or by catalytic reduction. The catalytic reduction is usually carried out in the presence of a conventional catalyst, such as Raney nickel, palladium, platinum, rhodium, copper, etc. preferably at ambient temperature under atmospheric pressure and in a conventional solvent. The reduction using a reducing agent is usually carried out in a conventional solvent, preferably a polar solvent, such as water, alcohol, and the like.

The present reaction can be conducted under cooling or slightly elevated temperature.

Process 5

The compound [I] and its salt can be prepared by reducing the compound [If] or its salt. The reduction can be conducted similarly to that of the second step of Process 4.

Process 6

The compound [Ih] and its salt can be prepared by reacting the compound [Ig] or its salt with an halogenating agent. Suitable halogenating agent may include chlorine, bromine, iodine, N-bromosuccinimide, N-chlorosuccinimide and the like. The reaction is usually conducted in a conventional solvent as exemplified in Process 1 under cooling or warming.

Process 7

The compound [Ij] and its salt can be prepared by subjecting the compound [Ii] or its salt to an elimination reaction of the protective group. The elimination reaction of the protective group can be conducted by a solvolysis (e.g., hydrolysis, aminolysis, alcoholysis, etc.), hydrogenolysis, or the like according to a kind of the protective group.

Among these methods, in case of the protective group is an acyl group such as a lower alkanoyl, solvolysis in the presence of a base or an acid is one of the common and preferable methods. More preferably, aminolysis using hydrazine or ammonia is convenient.

In case of the protective group is a ar(lower)alkyl group, hydrolysis in the presence of an acid or reduction is one of the preferable methods. The reduction can be conducted in a similar manner to that of Process 4, more preferably, by catalytic reduction. Suitable acid to be used in hydrolysis may include hydrogen halide (e.g. hydrogen iodide, hydrogen bromide, etc.), boron trihalide (e.g. boron tribromide, boron trichloride, etc.) and the like.

The present reaction can be conducted under cooling to heating in a conventional solvent which does not adversely influence the reaction such as water, alcohol, dichloromethane, chloroform and the like.

Process 8

The compound [Iw] and its salt can be prepared by solvolysis of the compound [Ik] or its salt. This solvolysis can be conducted in a similar manner to that of Process 7.

Process 9

The compound [Im] and its salt can be prepared by reacting a compound [Iw] or its salt with an alkylating agent.

Suitable alkylating agent may include a lower alkyl halide such as lower alkyl chloride (e.g. propyl chloride, butyl chloride, etc.), lower alkyl bromide (e.g. methyl bromide, ethyl bromide, propyl bromide, etc.) lower alkyl iodide (e.g. methyl iodide, ethyl iodide, propyl iodide, etc.), lower alkylsulfate (e.g. dimethylsulfate, diethylsulfate, etc.), lower alkane sulfonate (e.g. methyl mesylate, ethyl mesylate, etc.), lower alkane tosylate (e.g. methyltosylate, ethyl tosylate, etc.) and the like.

The reaction is usually carried out in a solvent such as alcohol (e.g. methanol, ethanol, propanol, etc.), at room temperature or under warming, and preferably in the presence of a base such as alkali metal hydroxide (e.g. sodium hydroxide, potassium hydroxide, etc.), alakli metal alkoxide (e.g. sodium methoxide, potassium methoxide, etc.), alkali metal hydride (e.g. sodium hydride, potassium hydride, etc.) and the like.

Process 10

The compound [In] and its salts can be prepared by reacting the compound [III] or its salt with ammonia.

This reaction is usually conducted in a solvent such as water, alcohol (e.g. methanol, ethanol, isopropyl alcohol, etc.) and the like. This reaction is conducted at ambient temperature or under heating.

The starting compounds of the above processes contain new and known compounds and the new compounds can be prepared by the methods as shown in the Examples or the methods chemically equivalent thereto.

The salts of the starting compounds are exemplified the ones as the salts of compounds [I].

The object compounds [I] obtained in the above Process 1 to 10 can be isolated and purified in a conventional manner, for example, extraction, precipitation, fractional chromatography, fractional crystallization, recrystallization, and the like.

The object compound [I] thus prepared can be transformed into a pharmaceutically acceptable salt by a conventional method, if desired.

In case that the object compound [I] is a mixture of the optical isomers, optical resolution can optionally be conducted by conventional method.

The following antihypertensive testa data, inhibitory activity test data on platelet aggregation and antiulcer test data show that the compound [I] of the present invention exhibit antihypertensive activity, inhibitory activity on platelet aggregation and antiulcer activity, and are useful as antihypertensive agents for treating hypertension and as antithrombotic agents for treating thrombosis and also as antiulcer drugs for treating ulcer in animals and human beings.

Test method A

Five-week old male Wister rats were uninephrectomized under anesthesia. Deoxycorticosterone acetone (DOCA) (30 mg/kg), suspended in peanut oil, was injected subcutaneously twice a week and 1% saline was substituted for the drinking water. Animals with mean blood pressure 150-200 mmHg were used for experiment between 5 and 7 weeks after surgery.

The test compounds were administered orally.

Blood pressure was measured at the femoral artery by means of a pressure transducer and recorded as electrically integrated values of mean arterial pressure.

Test Compound

Example 1-(3)
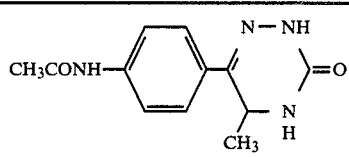

Example 6
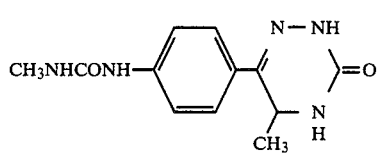

Example 24-(4) and Example 25-(3)
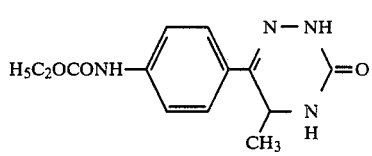

Example 24-(10) and Example 25-(9)
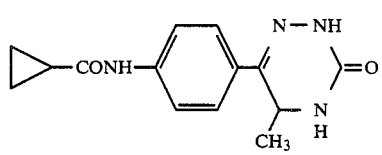

Test results A

Mean ratios of maximum decrease of blood pressure (mmHg) were shown in the following table.

| Test Compound (Example No.) | Dose | Effect Max (%) |
| --- | --- | --- |
| 1-(3) | a | 48.9 |
|  | b | 19.2 |
| 6 | a | 43.1 |
|  | b | 6.6 |
| 24-(4) | a | 54.5 |
| 25-(3) | b | 28.6 |
| 24-(10) 25-(9) | b | 41.1 | a: The test compound were administered orally in a dose of 1 mg/kg.
b: The test compound were administered orally in dose of 0.1 mg/kg.

Test Method B

Platelet rich plasma (PRP) which contains $6.5\text{-}7.5 \times 10^8$ platelet/ml was prepared from rabbit blood. To the 200 ul of PRP, 5 μl of calcium chloride (1 mM) and 50 μl of pH 7.4 Tris-acetate solution (5 mM) containing 120 mM NaCl and test compound were added successively, and then stirred for 2 min. at 37° C. To the solution, 5 μl of adenosine diphosphate (ADP) (2.5 μM) or collagen (2.5 ug/ml) was added as an aggregation inducer. Aggregation was measured by using an aggregometer (NKK HEMA TRACER 1). $ID_{50}$ was shown in Table 2.

Test results B

| Test Compound (Example No.) | $ID_{50}$ (Mol) ADP | Collagen |
| --- | --- | --- |
| 1-(3) | $6.2 \times 10^{-7}$ | $2.2 \times 10^{-7}$ |
| 6 | $7.4 \times 10^{-7}$ | $4.1 \times 10^{-7}$ |
| 24-(4), 25-(3) | $3.8 \times 10^{-7}$ | $6.9 \times 10^{-8}$ |
| 24-(10), 25-(9) | $3.4 \times 10^{-8}$ | $3.1 \times 10^{-9}$ |

Test methods C

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm²) in the medicated group was compared with that in the control group.

Test Compound

Example 23-(3)

CH₃CONH— [benzene ring]—C(=N-NH-C(=S)-NH)—CH₃

Test results C

| Test Compound (Example No.) | Dose (mg/kg) | Effect (%) |
| --- | --- | --- |
| 23-(3) | 32 | 87.0 |

As being apparent from the above test results, the object compounds [I] of the present invention are useful for antihypertensive medicines, antithrombotic medicines and antiulcer medicines.

The effective ingredient may usually be administered with a dose of 0.01 mg/kg to 500 mg/kg, 1 to 4 times a day in preparations such as tablet, granule, powder, capsule, syrup, injection, suppository and the like. However, the above dosage may be increased or decreased according to the age, weight or conditions of the patient or the administering method.

The pharmaceutical preparation may be prepared in a conventional manner.

The following Examples are given only for the purpose of illustrating the present invention in more detail.

EXAMPLE 1

(1) A mixture of 4'-acetamido-2-hydroxyiminopropiophenone (1.87 g), thiosemicarbazide (1 g), methanol (15 ml), water (3 ml) and acetic acid (0.1 ml) was refluxed with stirring for 39 hours and then cooled. The resulting precipitate was collected by filtration, washed with methanol and dried to give 4'-acetamido-2-hydroxyiminopropiophenone thiosemicarbazone (1.7 g).

NMR(DMSO—d$_6$,δ):2.08(3H,s),2.17 (3H,s),7.18(2H,d,J = 8Hz), 7.73(2H,d,J = 8Hz),8.13(1H, b.s.),8.63(2H,b.s.), 9.10(b.s.) } (1H), 11.69(s) } (1H)
10.23(b.s.) 12.26(s)

(2) A mixture of the compound (34.74 g) obtained by the above procedure (1), potassium carbonate (35.88 g) and water (300 ml) was refluxed with stirring for 3 hours. After cooling, sodium chloroacetate (20.6 g) was added, and the mixture was stirred at room temperature for 2 hours. The reaction mixture was washed with chloroform, acidified with hydrochloric acid and allowed to stand with cooling overnight. The thus-produced crystals were collected by filtration and washed with water to give 6-(4-acetamidophenyl)-3-carboxymethylthio-5-methyl-1,2,4-triazine (16.7 g).

NMR(DMSO-d$_6$, δ): 2.10(3H, s), Ca. 2.5 (3H, s), 3.96(2H, s), 7.58(2H, d, J=8 Hz), 7.77(2H, d, J=8 Hz), 10.35(1H, s).

(3) A mixture of the compound (10.61 g) obtained by the above procedure (2), 10% aqueous potassium hydroxide (46 ml) and methanol (45 ml) was heated with stirring at 60° C. for 2 hours. With cooling and stirring, sodium borohydride (1.64 g) was added in small portions to the above solution. The mixture was further stirred at room temperature for an hour and treated with 10% HCl to decompose the excess sodium borohydride, followed by concentration. The resulting precipitate was collected by filtration, washed with water and dried to give 6-(4-acetamidophenyl)-5-methyl-4,5-dihydro-1,2,4-triazin-3(2H)-one (6.12 g).

m.p. 272°-273° C. (recrystallized from 60% ethanol).

NMR(DMSO-d$_6$, δ): 1.22(3H, d, J=7 Hz), 2.08(3H, s), 4.64(1H, m), 7.43(1H, b.s.), 7.68(4H, s), 9.96(1H, d, J=2 Hz), 10.10(1H, s).

Elemental analysis: Calcd. for $C_{12}H_{14}N_4O_2 \cdot H_2O$: C, 54.54; H, 6.10; N, 21.20. Found: C, 54.87; H, 6.00; N, 21.45.

(4) A mixture of the compound (3.35 g) obtained by the above procedure (3) and 100% hydrazine hydrate (33 ml) was heated with stirring at 120° C. for 2 hours and allowed to stand at room temperature overnight. The resulting crystals were collected by filtration, washed with methanol and dried. The filtrate was concentrated under reduced pressure and the residue was crystallized from methanol. The first and second crops were combined and recrystallized from 60% aqueous ethanol to give 6-(4-aminophenyl)-5-methyl-4,5-dihydro-1,2,4-triazin-3(2H)-one (1.61 g).

m.p. 248°-249.5° C.

NMR(DMSO-d$_6$, δ): 1.16(3H, d, J=7 Hz), 4.52(1H, d, q, J=3.5, 7 Hz), 5.41(2H, s), 6.58(2H, d, J=8 Hz), 7.23(1H, b.s.), 7.42(2H, d, J=8 Hz), 9.67(1H, d, J=2 Hz).

Elemental analysis: Calcd. for $C_{10}H_{12}N_4O$: C, 58.81; H, 5.92; N, 27.44. Found: C, 58.64; H, 5.96; N, 27.33.

EXAMPLE 2

(1) 3'-Acetamido-4'-chloro-2-hydroxyiminopropiophenone (70.75 g) was reacted with thiosemicarbazide (28.4 g) in the same manner as Example 1-(1) to give 3'-acetamido-4'-chloro-2-hydroxyiminopropiophenone thiosemicarbazone (84.36 g).

NMR(DMSO-d$_6$, δ): 2.13(3H, s), 2.17 (3H, s), 7.03(1H, d, d, J=2, 8 Hz), 7.63(1H, d, J=8 Hz), 7.65(1H, d, J=2 Hz), 7.95~8.26(1H, m), 8.43~8.90(2H, m), 9.53(1H, m), 11.74(1H, s).

(2) A mixture of the compound (84.36 g) obtained by the above procedure (1), sodium carbonate (84.36 g), water (500 ml) and methanol (250 ml) was refluxed with stirring for 2 hours. After addition of water (1000 ml), methyl iodide (82.2 g) was added dropwise with stirring at room temperature, followed by further stirring for 30 minutes. The resulting precipitate was collected by filtration, washed with water and dried to give 6-(3-acetamido-4-chlorophenyl)-5-methyl-3-methylthio-1,2,4-triazine (64.13 g).

NMR(CDCl$_3$, δ): 2.27(3H, s), 2.61(3H, s), 2.70(3H, s), 7.26~7.64(2H, m), 7.68~7.94(1H, m), 8.56~8.67(1H, m).

(3) The compound (56.6 g) obtained by the above procedure (2) was worked up in the same manner as Example 1-(3) to give 6-(3-acetamido-4-chlorophenyl)-5-methyl-4,5-dihydro-1,2,4-triazin-3(2H)-one (38.68 g).

m.p. 251°-253° C. (recrystallized from aqueous ethanol).

NMR(DMSO-d$_6$, δ): 1.21(3H, d, J=7 Hz), 2.11(3H, s), 4.58(1H, d, q, J=3, 7 Hz), 7.47(3H, s), 8.06~8.19(1H, m), 9.45~9.56(1H, m), 10.03~10.18(1H, m).

Elemental analysis: Calcd. for $C_{12}H_{13}ClN_4O_2$: C, 51.34; H, 4.67; N, 19.96. Found: C, 51.36; H, 4.67, N, 19.86.

EXAMPLE 3

(1) A mixture of 2'-hydroxypropiophenone (25.8 g), benzyl chloride (21.8 g), sodium iodide (2.6 g), potassium carbonate (23.8 g) and dry dimethylformamide (260 ml) was heated with stirring at 80° C. for 23 hours. The mixture was cooled and filtered and the filtrate was concentrated under reduced pressure. The residue was extracted with ether and the extract was washed with water, 1N aqueous sodium hydroxide, water, 10% hydrochloric acid, aqueous sodium hydrogen carbonate and aqueous sodium chloride in that order, dried, and concentrated to dryness to give 2'-benzyloxypropiophenone (37.9 g) as an oil.

IR (neat): 1670 cm$^{-1}$.

NMR(CCl$_4$, δ): 1.06(3H, t, J=7 Hz), 2.88(q, 2H, J=7 Hz), 5.08(2H, s), 6.95(2H, m), 7.30(1H, m and 5H, s), 7.60(1H, dd, J=8 Hz, 2 Hz).

(2) With cooling, HCl gas was bubbled into a solution of the compound (37.8 g) obtained by the above procedure (1) in dry diethyl ether (120 ml), and isoamyl nitrite (22.2 g) was added dropwise over a period of 20 minutes. The mixture was further stirred for 2 hours, concentrated under reduced pressure and dissolved in a mixture of diethyl ether and hexane. The solution was extracted with 1N aqueous sodium hydroxide and the extract was acidified with 10% hydrochloric acid, followed by extraction with chloroform. The extract was washed with water, dried and concentrated to dryness under reduced pressure. The residue was crystallized from hexane to give 2'-benzyloxy-2-hydroxyiminopropiophenone (33.1 g).

m.p. 78°-80° C. (recrystallized from isopropyl ether-hexane).

IR (Nujol) 3230, 1690, 1600 cm$^{-1}$.

NMR(CDCl$_3$, δ): 1.94(3H, s), 4.89(2H, s), 6.9(3H, m), 7.23(5H, s), 7.35(1H, m), 8.55(1H, b.s.).

(3) A mixture of the compound (32.3 g) obtained by the above procedure (2), thiosemicarbazide (12.0 g), methanol (130 ml) and concentrated hydrochloric acid (1 ml) was refluxed with stirring for 4.5 hours. After cooling, the resulting precipitate was collected by filtration, washed with methanol and dried to give 2′-benzyloxy-2-hydroxyiminopropiophenone thiosemicarbazone (36.37 g).

m.p. 212°–213° C. (decomposition).

(4) The compound (10.0 g) obtained by the above procedure (3) was worked up in the same manner as Example 2-(2) to give 6-(2-benzyloxyphenyl)-5-methyl-3-methylthio-1,2,4-triazine (4.35 g).

IR(Neat) 3070,3030,2970,2920,2860,1600,1580,1495 cm$^{-1}$.

NMR(CDCl$_3$, δ): 2.36(3H, s), 2.70(3H, s), 5.07(2H, s), 7.0∼7.6(9H, m).

(5) The compound (4.3 g) obtained by the above procedure (4) was worked up in the same manner as Example 1-(3) to give 6-(2-benzyloxyphenyl)-5-methyl-4,5-dihydro-1,2,4-triazin-3(2H)-one (4.07 g).

m.p. 200°–203° C. (recrystallized from DMF-ethanol)
IR 3220,3080,1695 cm$^{-1}$.

NMR(DMSO-d$_6$): 1.07(3H, d, J=7 Hz), 4.55(1H, m), 5.20(2H, s), 7.0∼7.7(10H, m), 9.92(1H, s).

Elemental analysis: Calcd. for C$_{17}$H$_{17}$N$_3$O$_2$: C, 69.13; H, 5.80; N, 14.23. Found: C, 68.90; H, 5.83; N, 14.13.

(6) The compound (3.1 g) obtained by the above procedure (5) was dissolved in acetic acid (50 ml) and 10% palladium on carbon (3.1 g) was added. The mixture was stirred under hydrogen gas at 2.5 atmospheres at room temperature for 8.5 hours and then filtered. The filtrate was concentrated to dryness under reduced pressure to give 6-(2-hydroxyphenyl)-5-methyl-4,5-dihydro-1,2,4-triazin-3(2H)-one (1.37 g).

m.p. 257°–261° C. (recrystallized from DMF-ethanol).

IR(Nujol) 3210,3090,1700 cm$^{-1}$.

NMR(DMSO, d$_6$): 1.25(3H, d, J=7.5 Hz), 4.75(1H, m), 6.90(2H, m), 7.2∼7.6(3H, m), 10.13(1H, b.s.), 11.53(1H, s).

Elemental analysis: Calcd. for C$_{10}$H$_{11}$N$_3$O$_2$: C, 58.53; H, 5.40; N, 20.48. Found: C, 58.33; H, 5.13; N, 20.49.

EXAMPLE 4

With ice-cooling, butyric anhydride (1.76 g) was added gradually to a solution of 6-(4-aminophenyl)-5-methyl-4,5-dihydro-1,2,4-triazin-3(2H)-one (2.07 g) in pyridine (90 ml). The mixture was stirred at room temperature for 4 hours and concentrated under reduced pressure. To the residue was added diluted hydrochloric acid and the resulting crystals were collected by filtration, washed with water, dried and recrystallized from 50% aqueous ethanol to give 6-(4-butyrylaminophenyl)-5-methyl-4,5-dihydro-1,2,4-triazin-3(2H)-one (2.15 g).

m.p. 232°–234° C.

NMR(DMSO-d$_6$, δ): 0.92(3H, t, J=7 Hz), 1.21(3H, d, J=7 Hz), 1.64(2H, sixtet, J=7 Hz), 2.34(2H, t, J=7 Hz), 4.64(1H, d, q, J=3.5, 7 Hz), 7.40(1H, b.s.), 7.68(4H, s). 9.8∼10.1(2H, m).

EXAMPLE 5

With ice-cooling and stirring, a solution of tetradecanoyl chloride (2.83 g) in dimethylformamide (25 ml) was added dropwise to a solution of 6-(4-aminophenyl)-5-methyl-4,5-dihydro-1,2,4-triazin-3(2H)-one (2.34 g) and N,N-dimethylaniline (1.53 g) in dimethylformamide (23 ml) over a period of 10 minutes. After completion of the addition, the mixture was stirred at room temperature for an additional 1.5 hours. The solvent was then distilled off under reduced pressure and 10% hydrochloric acid was added to the residue. The resulting crystalline powder was collected by filtration, washed with water and dried to give 6-(4-tetradecanoylaminophenyl)-5-methyl-4,5-dihydro-1,2,4-triazin-3(2H)-one (3.82 g).

m.p. 206°–209° C. (recrystallized from ethanol).

IR (Nujol) 3300, 3200, 3100, 1725, 1660 cm$^{-1}$.

NMR (DMSO-d$_6$, δ): 0.84(3H, t, J=5 Hz), 1.0–2.0(25H, m), 2.31(2H, t, J=6 Hz), 4.59(1H, d, q, J=3 Hz, 7 Hz), 7.35(1H, s), 7.61(4H, s), 9.89(2H, s).

Elemental analysis: Calcd. for C$_{24}$H$_{38}$N$_4$O$_2$: C, 69.53; H, 9.24; N, 13.51. Found: C, 69.25; H, 9.23; N, 12.67.

EXAMPLE 6

A mixture of 6-(4-aminophenyl)-5-methyl-4,5-dihydro-1,2,4-triazin-3(2H)-one (1.5 g), methyl isocyanate (0.48 ml) and pyridine (40 ml) was stirred at room temperature for 4.5 hours, and ethanol (5 ml) was added. The solvent was then distilled off under reduced pressure. To the oily residue was added 10% HCl, and the thus-produced crystals were collected by filtration, washed with water, dried and recrystallized from aqueous dimethylformamide to give 6-[4-(3-methylureido)-phenyl]-5-methyl-4,5-dihydro-1,2,4-triazin-3(2H)-one (1.43 g).

m.p. 145°–150° C. (decomposition)

NMR(DMSO-d$_6$, δ): 1.22(3H, d, J=6.4 Hz), 2.69(3H, d, J=4.4 Hz), 4.63(1H, d, q, J=3, 6.4 Hz), 6.10(1H, q, J=4.4 Hz), 7.35(1H, b.s.), 7.45 (2H, d, J=9.6 Hz), 7.66(2H, d, J=9.6 Hz), 8.69(1H, s), 9.90(1H, b.s.).

EXAMPLE 7

6-(4-Aminophenyl)-5-methyl-4,5-dihydro-1,2,4-triazin-3(2H)-one (1.5 g) was reacted with phenyl isocyanate (0.88 ml) in the same manner as Example 6 to give 6-[4-(3-phenylureido)phenyl]-5-methyl-4,5-dihydro-1,2,4-triazin-3(2H)-one (1.26 g).

m.p. >140° C. (decomposition, recrystallized from aqueous dimethylformamide)

NMR(DMSO-d$_6$, δ): 1.22(3H, d, J=7 Hz), 4.64(1H, d, q, J=3, 7 Hz), 6.8∼7.9(10H, m), 8.70(1H, s), 8.84(1H, s), 9.92(1H, b.s.).

EXAMPLE 8

A solution of 6-(4-aminophenyl)-5-methyl-4,5-dihydro-1,2,4-triazin-3(2H)-one (3 g) and phenyl isothiocyanate (1.8 ml) in dimethylformamide (30 ml) was stirred at room temperature for 6 hours and then concentrated under reduced pressure. To the residue was added water and the thus-produced crystals were recovered by filtration, washed with water and dried to give 6-[4-(3-phenyl-thioureido)phenyl]-5-methyl-4,5-dihydro-1,2,4-triazin-3(2H)-one (5.32 g).

IR(Nujol) 3200,3080,1700,1680 cm$^{-1}$.

NMR(DMSO-d$_6$, δ): 1.22(3H, d, J=6.4 Hz), 4.66(1H, m), 7.0∼8.0(10H, m), 9.87(3H, b.m.).

EXAMPLE 9

A solution of 6-(4-aminophenyl)-5-methyl-4,5-dihydro-1,2,4-triazin-3(2H)-one (2 g) and methylisothiocyanate (0.788 g) in dimethylformamide (20 ml) was heated with stirring at 110° C. for 4 hours, followed by after-treatment in the same manner as Example 8 to give 6-[4-(3-methyl-thioureido)phenyl]-5-methyl-4,5-dihydro-1,2,4-triazin-3(2H)-one (2.7 g).

IR(Nujol) 3215,3060,1680,1670 cm$^{-1}$.

NMR(DMSO-d$_6$, δ): 1.21(3H, d, J=6.6 Hz), 2.53(3H, d, J=2 Hz), 4.63(1H, d, q, J=2, 6.6 Hz), 7.1~8.1(6H, m), 9.68(1H, b.s.), 9.91(1H, b.s.).

EXAMPLE 10

With ice-cooling and stirring, acetic anhydride (1.4 ml) was added dropwise to formic acid (0.7 ml) and the mixture was stirred at 50° C. for 15 minutes. This solution was added to a solution of 6-(4-aminophenyl)-5-methyl-4,5-dihydro-1,2,4-triazin-3(2H)-one (2.28 g) in formic acid (6 ml) with ice-cooling and stirring, followed by further stirring with ice-cooling for 50 minutes. The reaction mixture was poured into ice water and the resulting precipitate was collected by filtration and washed with water. The solid was recrystallized from dimethyl sulfoxide to give 6-(4-formylaminophenyl)-5-methyl-4,5-dihydro-1,2,4-triazin-3(2H)-one (1.36 g).

m.p. 258°–263° C. (decomposition).

NMR(DMSO—d$_6$,δ):1.24(3H,d,J = 6.6Hz),
4.64(1H,d,q,J = 3,6.6Hz),
7.39(1H,b.s.),7.62(4H,s), 8.29(b.s.)
8.81(d,J = 10.2Hz) } (1H), 9.92(1H,b.s.), 10.15(d,J = 10.2Hz)
10.23(b.s.) } (1H)

Elemental analysis: Calcd. for C$_{11}$H$_{12}$N$_4$O$_2$: C, 56.89; H, 5.21. Found: C, 56.68; H, 5.32.

EXAMPLE 11

A solution of 6-(4-acetamidophenyl)-5-methyl-4,5-dihydro-1,2,4-triazin-3(2H)-one (0.5 g) and N-chlorosuccinimide (0.41 g) in dimethylformamide (7 ml) was stirred at 40° C. for 3 hours and then poured into water. The thus-produced crsytals were collected by filtration, washed with water and dried to give 6-(4-acetamido-3-chlorophenyl)-5-methyl-4,5-dihydro-1,2,4-triazin-3(2H)-one (0.331 g).

m.p. 250°–252° C. (recrystallized from methanol).

NMR(DMSO-d$_6$, δ): 1.22(3H, d, J=6.2 Hz), 2.13(3H, s), 4.65(1H, m), 7.47 (1H, b.s.), 7.60(1H, d, d, J=2,8 Hz), 7.80(1H, d, J=2 Hz), 7.86(1H, d, J=8 Hz), 9.49(1H, b.s.), 10.04(1H, b.s.).

EXAMPLE 12

A mixture of 6-(4-aminophenyl)-5-methyl-4,5-dihydro-1,2,4-triazin-3(2H)-one (0.2 g), N-chlorosuccinimide (0.135 g) and dimethylformamide (3 ml) was stirred with ice-cooling for an hour. The reaction mixture was poured into water and extracted with chloroform. The extract was concentrated to dryness under reduced pressure and the residue was crystallized from chloroform to give 6-(4-amino-3-chlorophenyl)-5-methyl-4,5-dihydro-1,2,4-triazin-3(2H)-one (0.02 g).

m.p. 229°–231° C. (recrystallized from methanol)

NMR(DMSO-d$_6$, δ): 1.16(3H, d, J=6.6 Hz), 4.52(1H, m), 5.64(2H, s), 6.77 (1H, d, J=8 Hz), 7.25(1H, b.s.), 7.38(1H, d, d, J=2, 8 Hz), 7.53 (1H, d, J=2 Hz), 9.73(1H, b.s.).

EXAMPLE 13

6-(4-Aminophenyl)-5-methyl-4,5-dihydro-1,2,4-triazin-3(2H)-one (5 g) was reacted with N-bromosuccinimide (4.36 g) in the same manner as Example 12 to give 6-(4-amino-3-bromophenyl)-5-methyl-4,5-dihydro-1,2,4-triazin-3(2H)-one (5.76 g).

m.p. 222°–224° C. (recrystallized from ethanol).

NMR(DMSO-d$_6$, δ): 1.16(3H, d, J=6.6 Hz), 4.53(1H, m), 5.62(2H, s), 6.77 (1H, d, J=8 Hz), 7.27(1H, b.s.), 7.43(1H, d, d, J=2,8 Hz), 7.67 (1H, d, J=2 Hz), 9.76(1H, b.s.).

EXAMPLE 14

6-(4-Benzyloxyphenyl)-5-methyl-4,5-dihydro-1,2,4-triazin-3(2H)-one (1.5 g) obtained by the procedure of Examples 3-(1) to 3-(5) was dissolved in acetic acid (36 ml) and the hydrogenolysis reaction was carried out with 5% palladium on carbon (1.6 g) at atmospheric pressure and room temperature. After the theoretical amount of hydrogen gas had been absorbed, the catalyst was filtered off and the filtrate was concentrated to dryness under reduced pressure. To the residue was added water and the solid which formed was collected and recrystallized from 90% ethanol to give 6-(4-hydroxyphenyl)-5-methyl-4,5-dihydro-1,2,4-triazin-3(2H)-one (0.42 g).

m.p. 256°–259° C.

NMR(DMSO-d$_6$, δ): 1.19(3H, d, J=7.2 Hz), 4.57(1H, d, q, J=3.8, 7.2 Hz), 6.80(2H, d, J=8.4 Hz), 7.31(1H, b.s.), 7.56(2H, d, J=8.4 Hz), 9.6~9.8(2H, m).

Elemental analysis: Calcd. for C$_{10}$H$_{11}$N$_3$O$_2$: C, 58.53; H, 5.40; N, 20.48. Found: C, 58.41; H, 5.28; N, 20.50.

EXAMPLE 15

6-[4-(4-Benzyloxyphenylacetamido)phenyl]-5-methyl-4,5-dihydro-1,2,4-triazin-3(2H)-one (3.63 g) was worked up in the same manner as Example 14 to give 6-[4-(4-hydroxyphenylacetamido)phenyl]-5-methyl-4,5-dihydro-1,2,4-triazin-3(2H)-one (2.27 g).

IR(Nujol) 3230, 3180, 3090, 1690, 1660 cm$^{-1}$.

NMR(DMSO-d$_6$, δ): 1.20(3H, d, J=6.2 Hz), 3.53(2H, s), 4.61(1H, m), 6.70 (2H, d, J=8.2 Hz), 7.14(2H, d, J=8.2 Hz), 7.36(1H, b.s.), 7.63 (4H, s), 9.21(1H, s), 9.90(1H, b.s.), 10.16(1H, b.s.).

EXAMPLE 16

A mixture of 6-(3-acetamido-4-chlorophenyl)-5-methyl-4,5-dihydro-1,2,4-triazin-3(2H)-one (34.75 g) and 100% hydrazine hydrate (100 ml) was heated at 100° C. for 3 hours. After cooling, the resulting crystals were recovered by filtration and washed with aqueous methanol to give 6-(3-amino-4-chlorophenyl)-5-methyl-4,5-dihydro-1,2,4-triazin-3(2H)-one (28.04 g).

m.p. 226°–228.5° C. (recrystallized from aqueous ethanol).

NMR(DMSO-d$_6$, δ): 1.18(3H, d, J=6.5 Hz), 4.52(1H, d, q, J=3, 6.5 Hz), 5.27~5.60(2H, m), 6.88(1H, d, d, J=2, 8.4 Hz), 7.22(1H, d, J= 2 Hz), 7.24(1H, d, J=8.4 Hz), 7.30~7.49(1H, m), 9.92~10.07 (1H, m).

Elemental analysis: Calcd. for C$_{10}$H$_{11}$ClN$_4$O: C, 50.32; H, 4.65; N, 23.47. Found: C, 50.46; H, 4.55; N, 23.59.

EXAMPLE 17

6-(4-Acetamido-3-chlorophenyl)-5-methyl-4,5-dihydro-1,2,4-triazin-3(2H)-one (0.388 g) was worked up in the same manner as Example 16 to give 6-(4-amino-3-chlorophenyl)-5-methyl-4,5-dihydro-1,2,4-triazin-3(2H)-one (0.21 g).

m.p. 229°–231° C. (recrystallized from methanol)

NMR(DMSO-$d_6$, $\delta$): 1.16(3H, d, J=6.6 Hz), 4.52(1H, m), 5.64(2H, s), 6.77 (1H, d, J=8 Hz), 7.25(1H, b.s.), 7.38 (1H, d, d, J=2, 8 Hz), 7.53 (1H, d, J=2 Hz), 9.73(1H, b.s.).

EXAMPLE 18

(1) With cooling and stirring, a solution of sodium nitrite (3.97 g) in water (12 ml) was added dropwise to a mixture of 6-(4-aminophenyl)-5-methyl-4,5-dihydro-1,2,4-triazin-3(2H)-one (11.18 g), concentrated hydrochloric acid (12 ml) and water (48 ml). After completion of the addition, the reaction mixture containing the corresponding diazonium salt was added dropwise to a solution of potassium O-ethyldithiocarbonate (10.62 g) in water (13 ml) with stirring at 40°–45° C. over a period of an hour. The reaction mixture was further stirred at the same temperature for 1.5 hours and extracted with dichloromethane. The extract was washed with water, 1N aqueous sodium hydroxide and water in that order, dried and concentrated to dryness under reduced pressure. The residue was purified by silica gel (130 g) column chromatography [eluent: chloroform-methanol (20:1)] to give 6-[4-[ethoxy(thiocarbonyl)thio]phenyl]-5-methyl-4,5-dihydro-1,2,4-triazin-3(2H)-one (7.0 g).

NMR(CDCl$_3$, $\delta$): 1.34(3H, t, J=7 Hz), 1.42(3H, d, J=7 Hz), 4.63(2H, q, J=7 Hz), 4.74(1H, d, q, J=3,7 Hz), 6.85~7.16(1H, m), 7.50(2H, d, J=9 Hz), 7.74(2H, d, J=9 Hz), 8.80~9.13(1H, m).

(2) A mixture of the compound (6.5 g) obtained by the above procedure (1), potassium hydroxide (2.66 g) and methanol (50 ml) was stirred at room temperature for 30 minutes and the solvent was distilled off under reduced pressure. The resulting solid was washed with ethyl acetate and methanol and dissolved in water. The solution was treated with activated carbon and acidified with acetic acid, and the crystals which formed were collected, washed with water and dried to give 6-(4-mercaptophenyl)-5-methyl-4,5-dihydro-1,2,4-triazin-3(2H)-one (3.31 g).

m.p. 202°–204° C. (recrystallized from 70% aqueous ethanol).

NMR(DMSO-$d_6$, $\delta$): 1.18(3H, d, J=6.5 Hz), 4.62(1H, d, q, J=35, 6.5 Hz), 5.40~5.75(1H, m), 7.17~7.90 (1H, m), 7.33(2H, d, J=8 Hz), 7.63(2H, d, J=8 Hz), 9.87~10.16 (1H, m).

Elemental analysis: Calcd. for $C_{10}H_{11}N_3OS$: C, 54.38; H, 5.01; N, 18.99. Found: C, 54.33; H, 4.83; N, 19.14.

(3) With stirring, methyl iodide (0.57 g) was added dropwise to a solution composed of the compound (0.64 g) obtained by the above procedure (2), saturated aqueous sodium carbonate (0.5 ml), methanol (3 ml) and water (6 ml), and the mixture was further stirred for 30 minutes. The crystals which formed were recovered by filtration and recrystallized from aqueous ethanol to give 6-(4-methylthiophenyl)-5-methyl-4,5-dihydro-1,2,4-triazin-3(2H)-one (0.48 g).

m.p. 210°–211° C.

NMR(DMSO-$d_6$, $\delta$): 1.20(3H, d, J=7 Hz), 2.48(3H, s), 4.62(1H, d, q, J= 3.7 Hz), 7.24(2H, d, J=9 Hz), 7.25~7.54(1H, m), 7.65(2H, d, J=9 Hz), 9.88~10.07(1H, m).

Elemental analysis: Calcd. for $C_{11}H_{13}N_3OS$: C, 56.15; H, 5.57; N, 17.86. Found: C, 55.99; H, 5.41; N, 17.65.

EXAMPLE 19

Using 6-(4-aminophenyl)-5-methyl-4,5-dihydro-1,2,4-triazin-3(2H)-one (1 g) in a similar manner to that of Example 18-(1), a diazonium salt-containing aqueous solution was produced. With stirring at 80° C., this solution was added dropwise to a solution composed of thiophenol (1.04 g), sodium hydroxide (0.45 g) and water (5 ml) and the mixture was refluxed for further 15 minutes. After cooling, the precipitate was recovered by filtration and dissolved in a mixture of chloroform and methanol. The solution was washed with aqueous sodium hydroxide and water in that order and concentrated to dryness under reduced pressure. The residue was purified by silica gel (30 g) column chromatography (eluent: ethyl acetate) to give 6-(4-phenylthiophenyl)-5-methyl-4,5-dihydro-1,2,4-triazin-3(2H)-one (0.46 g).

NMR(DMSO-$d_6$, $\delta$): 1.20(3H, d, J=7 Hz), 4.61(1H, d, q, J=3,7 Hz), 7.2~7.9(1H, m), 7.27(2H, d, J=9 Hz), 7.40(5H, s), 7.71(2H, d, J=9 Hz), 9.93~10.14(1H, m).

EXAMPLE 20

(1) In the same manner as Example 18-(1), there was produced a solution containing the diazonium salt derived from 6-(4-aminophenyl)-5-methyl-4,5-dihydro-1,2,4-triazin-3(2H)-one (4.08 g). With ice-cooling, the solution was added dropwise to a mixture composed of cupric chloride dihydrate (0.88 g), water (1.82 ml) and a saturated solution of sulfur dioxide in acetic acid (20 ml) over a period of 10 minutes. The mixture was stirred at 15° C. for 1.5 hours and filtered, and the filtrate was poured into ice water. The crystals which formed were recovered by filtration and dissolved in chloroform and the solution was concentrated to dryness under reduced pressure. The oily residue was crystallized from ethyl acetate to give 6-(4-chlorosulfonylphenyl)-5-methyl-4,5-dihydro-1,2,4-triazin-3(2H)-one (4.27 g).

NMR(CDCl$_3$, $\delta$): 1.45(3H, d, J=6.5 Hz), 4.75(1H, m), 6.33(1H, m), 7.90 (2H, d, J=9 Hz), 8.09(2H, d, J=9 Hz), 8.6(1H, m).

(2) A mixture of 6-(4-chlorosulfonylphenyl)-5-methyl-4,5-dihydro-1,2,4-triazin-3(2H)-one (4.27 g) and concentrated ammonium hydroxide (30 ml) was stirred at room temperature for 30 minutes and then at 50° C. for 1 hour, and concentrated under reduced pressure. To the residue was added water and the mixture was stirred with ice-cooling for 10 minutes. The crystals which formed were recovered by filtration, washed with water and recrystallized from aqueous ethanol to give 6-(4-sulfamoylphenyl)-5-methyl-4,5-dihydro-1,2,4-triazin-3(2H)-one (2.91 g).

m.p. 259°–264° C.

NMR(DMSO-$d_6$, $\delta$): 1.62(3H, d, J=6.5 Hz), 4.72(1H, d, q, J=3, 6.5 Hz), 7.35 (2H, m), 7.50(1H, m), 7.86(4H, s), 10.15(1H, m).

Elemental analysis: Calcd. for $C_{10}H_{12}N_4O_3S$: C, 44.77; H, 4.51; N, 20.88; S, 11.95. Found: C, 44.37; H, 4.43; N, 20.80; S, 12.02.

EXAMPLE 21

In the same manner as Example 18-(1), there was produced a solution containing the diazonium salt derived from 6-(3-amino-4-chlorophenyl)-5-methyl-4,5- dihydro-1,2,4-triazin-3(2)-one (4 g). With ice-cooling and stirring, the solution was added dropwise to a mixture of cupric chloride dihydrate (0.75 g), water (15 ml) and saturated solution of sulufur dioxide in acetic acid (20 ml) over a period of 20 minutes. The mixture was stirred at room temperature for 1.5 hours, poured into ice water and extracted with chloroform. The extract was washed with water, dried and concentrated to dryness under reduced pressure to give 6-(4-chloro-3-chlorosulfonylphenyl)-5-methyl-4,5-dihydro-1,2,4-triazin-3-(2H)-one (3.91 g). This compound was added to a solution of concentrated ammonium hydroxide (50 ml) in methanol (30 ml) and the mixture was heated with stirring at 50° C. for 20 minutes. The reaction mixture was concentrated to dryness under reduced pressure, and the residue was washed with water, dried and recrystallized from aqueous ethanol to give 6-(4-chloro-3-sulfamoylphenyl)-5-methyl-4,5-dihydro-1,2,4-triazin-3(2H)-one (1.96 g).

m.p. 275°–277° C.

NMR(DMSO-$d_6$, $\delta$): 1.21(3H, d, J=6.5 Hz), 4.67(1H, d, q, J=3, 6.5 Hz), 7.48~7.79(3H, m), 7.65(1H, d, J=8.5 Hz), 7.92(1H, d, d, J=2, 8.5 Hz), 8.38 (1H, d, J=2 Hz), 10.20~10.33 (1H, b.m.).

EXAMPLE 22

In the same manner as Example 18-(1), there was produced a solution containing the diazonium salt derived from 6-(4-aminophenyl)-5-methyl-4,5-dihydro-1,2,4-triazin-3(2H)-one (3.06 g). The solution was neutralized carefully with saturated aqueous sodium carbonate followed by addition of an ice-cooled solution of potassium cyanide (1.88 g) and cuprous cyanide (1.17 g) in water (12 ml). The mixture was stirred for an hour and the crystals which formed were recovered by filtration, washed with water, 1N aqueous sodium hydroxide, 1N hydrochloric acid and water in that order and dissolved in aqueous ethanol. The solution was treated with activated carbon and concentrated to dryness under reduced pressure. The residue was purified by silica gel (190 g) column chromatography [eluent: chloroform-methanol (20:1)] to give 6-(4-cyanophenyl)-5-methyl-4,5-dihydro-1,2,4-triazin-3(2H)-one (1.469 g).

m.p. 268°–269° C. (recrystallized from aqueous ethanol).

IR(Nujol) 2220 cm$^{-1}$.

NMR(DMSO-$d_6$, $\delta$): 1.22 (3H, d, J=6.8 Hz), 4.73 (1H, d, q, J=3.5, 6.8 Hz), 7.46~7.73 (1H, b.m.), 7.89 (4H, s), 10.16~10.43 (1H, b.m.).

Elemental analysis: Calcd. for $C_{11}H_{10}N_4O$: C, 62.10; H, 4.84; N, 26.41. Found: C, 61.67; H, 4.70; N, 26.15.

EXAMPLE 23

(1) A solution of 4'-acetamido-2-hydroxyiminopropiophenone thiosemicarbazone (5 g) and potassium carbonate (5.2 g) in water (40 ml) was refluxed for 24 hours and treated with activated carbon. The filtrate was acidified with diluted hydrochloric acid and the crystals which formed were recovered by filtration, washed with water and dried to give 6-(4-aminophenyl)-5-methyl-1,2,4-triazin-3(2H)-thione (2.69 g).

IR (Nujol) 3300, 3200, 1610, 1520, 1460, 1370 cm$^{-1}$.

(2) With ice-cooling, sodium borohydride (0.38 g) was added in small portions to a solution of the compound (2.6 g) obtained by the above procedure (1) in methanol (13 ml) plus tetrahydrofuran (13 ml). The mixture was stirred at the same temperature for an hour, acidified with 10% hydrochloric acid and concentrated under reduced pressure. The solid residue was washed with water, dried and recrystallized from dimethylformamide-ethanol-water (1:1:3) to give 6-(4-aminophenyl)-5-methyl-4,5-dihydro-1,2,4-triazin-3(2H)-thione (0.77 g).

IR (Nujol) 3450, 3310, 3180, 1620, 1590, 1560 cm$^{-1}$.

(3) The compound (0.7 g) obtained by the above procedure (2) was reacted with acetic anhydride (0.39 g) in the same manner as Example 4 to give 6-(4-acetamidophenyl)-5-methyl-4,5-dihydro-1,2,4-triazin-3(2H)-thione (0.51 g).

m.p. 222°–226° C. (recrystallized from ethanol)

IR(Nujol) 3170, 1690, 1600 cm$^{-1}$.

NMR(DMSO-$d_6$, $\delta$): 1.21 (3H, d, J=6.5 Hz), 2.09 (3H, s), 4.65 (1H, m), 7.77 (4H, s), 9.23 (1H, m), 10.18 (1H, s), 11.35 (1H, s).

Elemental analysis: Calcd. for $C_{12}H_{14}N_4OS$: C, 54.92; H, 5.38; N, 21.35; S, 12.22. Found: C, 54.49; H, 5.36; N, 21.43; S, 11.97.

EXAMPLE 24

In the same manner as Example 4 or 5, there were obtained the following compounds.

(1) 6-(4-Acetamidophenyl)-5-methyl-4,5-dihydro-1,2,4-triazin-3(2H)-one (yield 73.0%).

m.p. 272°–273° C.

NMR(DMSO-$d_6$, $\delta$): 1.22 (3H, d, J=7 Hz), 2.08 (3H, s), 4.64 (1H, m), 7.43 (1H, b.s.), 7.68 (4H, s), 9.96 (1H, d, J=2 Hz), 10.10 (1H, s).

(2) 6-(4-Methoxyacetamidophenyl)-5-methyl-4,5-dihydro-1,2,4-triazin-3(2H)-one (yield 74.9%).

m.p. 225.5°–228° C. (recrystallized from 70% aqueous ethanol).

IR (Nujol) 3390, 3210, 3080, 1700 (shoulder), 1685 cm$^{-1}$.

NMR(DMSO-$d_6$, $\delta$): 1.20 (3H, d, J=7.2 Hz), 3.38 (3H, s), 4.02 (2H, s), 4.62 (1H, d, q, J=3, 7.2 Hz), 7.38 (1H, b.s.), 7.62 (2H, d, J=8.2 Hz), 7.77 (2H, d, J=8.2 Hz), 9.84 (1H, b.s.), 9.91 (1H, d, J=2 Hz).

Elemental analysis: Calcd. for $C_{13}H_{16}N_4O_3$: C, 56.51; H, 5.84; N, 20.28. Found: C, 56.79; H, 5.82; N, 20.33.

(3) 6-(4-Isobutyrylaminophenyl)-5-methyl-4,5-dihydro-1,2,4-triazin-3(2H)-one (yield 23.5%).

m.p. 235°–239° C. (recrystallized from ethanol)

IR(Nujol) 3310, 3220, 3160, 3100, 3050, 1685 cm$^{-1}$.

NMR(DMSO-$d_6$, $\delta$): 1.10 (6H, d, J=6.4 Hz), 1.19 (3H, d, J=6.8 Hz), Ca. 2.4~2.8 (1H, m), 4.60 (1H, d, q, J=3.2, 6.8 Hz), 7.36 (1H, b.s.), 7.64 (4H, s), 9.90 (2H, b.s.).

Elemental analysis: Calcd. for $C_{14}H_{18}N_4O_2$: C, 61.30; H, 6.61; N, 20.42. Found: C, 61.39; H, 6.54; N, 20.73.

(4) 6-(4-Ethoxycarbonylaminophenyl)-5-methyl-4,5-dihydro-1,2,4-triazin-3(2H)-one.

m.p. 231°–235° C. (recrystallized from 80% aqueous ethanol).

NMR(DMSO-$d_6$, $\delta$): 1.1~1.5 (6H, complex), 4.15 (2H, q, J=6 Hz), 4.60 (1H, d, q, J=3.8, 6.2 Hz), Ca. 7.4 (1H, b.s.), 7.48 (2H, d, J=10 Hz), 7.68 (2H, d, J=10 Hz), 9.72 (1H, s), 9.86 (1H, b.s.).

Elemental analysis: Calcd. for $C_{13}H_{16}N_4O_3$: C, 56.51; H, 5.84; N, 20.28. Found: C, 56.54; H, 5.71; N, 20.33.

(5) 6-(4-Phenylacetamidophenyl)-5-methyl-4,5-dihydro-1,2,4-triazin-3(2H)-one (yield 67.7%)

m.p. 204°–207° C. (recrystallized from aqueous ethanol).

IR (Nujol) 3250, 3100, 1710, 1660 cm$^{-1}$.

NMR(DMSO-d$_6$, δ): 1.21 (3H, d, J=7 Hz), 3.68 (2H, s), 4.61 (1H, d, q, J=3, 7 Hz), 7.31 (5H, s), Ca. 7.4 (1H, b.s.), 7.65 (4H, s), 9.91 (1H, b.s.), 10.25 (1H, s).

Elemental analysis: Calcd. for C$_{18}$H$_{18}$N$_4$O$_2$: C, 67.67; H, 5.63; N, 17.38. Found: C, 66.63; H, 5.63; N, 17.20.

(6) 6-(4-Acryloylaminophenyl)-5-methyl-4,5-dihydro-1,2,4-triazin-3(2H)-one (yield 90.1%).

NMR(DMSO-d$_6$, δ): 1.20 (3H, d, J=7 Hz), 4.63 (1H, d, q, J=3,7 Hz), 5.76 (1H, d, d, J=4.5, 8.5 Hz), 6.35 (1H, d, J=4.5 Hz), 6.39 (1H, d, J=8.5 Hz), 7.29~7.51 (1H, m), 7.69 (4H, s), 9.85~10.01 (1H, m), 10.20~10.31 (1H, m).

(7) 6-(4-Crotonoylaminophenyl)-5-methyl-4,5-dihydro-1,2,4-triazin-3(2H)-one (yield 51.3%).

m.p. 259°-263° C. (decomposition) (recrystallized from 70% aqueous ethanol).

IR(Nujol) 3220, 3080, 1680, 1585 cm$^{-1}$.

NMR(DMSO-d$_6$, δ): 1.21 (3H, d, J=6.8 Hz), 1.88 (3H, d, J=6.4 Hz), 4.64 (1H, d, q, J=3.6, 6.8 Hz), 6.14 (1H, b.d. J=15.2 Hz), 6.85 (1H, d, q, J=15.2, 6.4 Hz), 7.39 (1H, b.s.), 7.69 (4H, s), 9.94 (1H, b.s.), 10.05 (1H, b.s.).

(8) 6-(3-Chloro-4-crotonoylaminophenyl)-5-methyl-4,5-dihydro-1,2,4-triazin-3(2H)-one (yield 17.8%).

m.p. 260°-264° C. (decomposition) (recrystallized from 70% aqueous ethanol).

IR(Nujol) 3400, 3200, 3080, 1700, 1690 cm$^{-1}$.

NMR(DMSO-d$_6$, δ): 1.21 (3H, d, J=7 Hz), 1.88 (3H, d, J=6.4 Hz), 4.65 (1H, d, q, J=3, 7 Hz), 6.31 (1H, b.d., J=15 Hz), 6.87 (1H, d, q, J=15, 6.4 Hz), 7.46 (1H, b.s.), 7.63 (1H, d, d, J=2, 8.4 Hz), 7.80 (1H, d, J=2 Hz), 7.93 (1H, d, J=8.4 Hz), 9.48 (1H, b.s.), 10.05 (1H, d, J=2 Hz).

Elemental analysis: Calcd. for C$_{14}$H$_{15}$ClN$_4$O$_2$: C, 54.82; H, 4.93; N, 18.26. Found: C, 54.53; H, 4.97; N, 18.33.

(9) 6-[4-(4-Benzyloxyphenylacetamido)phenyl]-5-methyl-4,5-dihydro-1,2,4-triazin-3(2H)-one (yield 36.6%).

IR(Nujol) 3210, 1710, 1660 cm$^{-1}$.

NMR(DMSO-d$_6$, δ): 1.20 (3H, d, J=6.2 Hz), 3.62 (2H, s), 4.62 (1H, m), 5.08 (2H, s), 6.96 (2H, d, J=8.4 Hz), 7.1~7.9 (12H, m), 9.92 (1H, b.s.), 10.30 (1H, b.s.).

(10) 6-(4-Cyclopropanecarbonylaminophenyl)-5-methyl-4,5-dihydro-1,2,4-triazin-3(2H)-one (yield 35.6%).

m.p. 288°-291° C. (recrystallized from aqueous dimethylformamide)

IR(Nujol) 3320, 3280, 3160, 3100, 1695, 1655 cm$^{-1}$.

NMR(DMSO-d$_6$, δ): 0.87 (4H, broad d, J=5.2 Hz), 1.27(3H, d, J=6.6 Hz), 1.86(1H, broad quintet, J=6 Hz), 4.66(1H, d, q, J=3.4, 6.6 Hz), 7.41(1H, b.s.), 7.66 (4H, s), 9.92(1H, b.s.), 10.28 (1H, b.s.).

Elemental analysis: Calcd. for C$_{14}$H$_{16}$N$_4$O$_2$: C, 61.75; H, 5.92; N, 20.57. Found: C, 61.72; H, 6.04; N, 20.63.

(11) 6-(4-Cyclobutanecarbonylaminophenyl)-5-methyl-4,5-dihydro-1,2,4-triazin-3(2H)-one (yield 32.1%).

m.p. 260°-262° C. (recrystallized from 70% aqueous ethanol).

IR(Nujol) 3300, 3200, 3090, 1686, 1672 cm$^{-1}$.

NMR(DMSO-d$_6$, δ): 1.17(3H, d, J=7 Hz), 1.5~2.5(6H, m), 3.20(1H, m), 4.62(1H, m), 7.37(1H, b.s.), 7.66(4H, s), 9.82(1H, b.s.), 9.91(1H, b.s.).

Elemental analysis: Calcd. for C$_{15}$H$_{18}$N$_4$O$_2$: C, 62.92; H, 6.34; N, 19.57. Found: C, 63.10; H, 6.33; N, 19.60.

(12) 6-[4-(1-Adamantanecarbonylamino)phenyl]-5-methyl-4,5-dihydro-1,2,4-triazin-3(2H)-one (yield 10.9%).

m.p. >300° C. (recrystallized from aqueous dimethylformamide)

NMR(DMSO-d$_6$, δ): 1.19(3H, d, J=7 Hz), 1.71(6H, b.s.), 1.92(9H, b.s.), 4.61(1H, d, q, J=3.7 Hz), 7.36 (1H, b.s.), 7.68(4H, s), 9.19 (1H, s), 9.89(1H, b.s.).

(13) 6-(4-Mesylaminophenyl)-5-methyl-4,5-dihydro-1,2,4-triazin-3(2H)-one.

m.p. 261°-264° C. (recrystallized from 70% aqueous ethanol)

NMR(DMSO-d$_6$, δ): 1.22(3H, d, J=6.6 Hz), 3.04(3H, s), 4.61(1H, d, q, J=3.4, 6.6 Hz), 7.22(2H, d, J=9 Hz), 7.3(1H, b.s.), 7.70(2H, d, J=9 Hz), 9.90(2H, b.s.).

Elemental analysis: Calcd. for C$_{11}$H$_{14}$N$_4$O$_3$S: C, 46.80; H, 5.00; N, 19.85. Found: C, 46.72; H, 4.86; N, 19.87.

(14) 6-[4-(2,3-Dimethylpentanoylamino)phenyl]-5-methyl-4,5-dihydro-1,2,4-triazin-3(2H)-one.

m.p. 242°-244° C. (recrystallized from ethanol).

IR (Nujol) 3330, 3200, 3100, 1690, 1665 cm$^{-1}$.

NMR (DMSO-d$_6$, δ): 0.66-1.8 (12H, m), 1.19 (3H, d, J=7 Hz), 2.1-2.5 (1H, m), 4.59 (1H, d, q, J=3 Hz, 7 Hz), 7.36 (1H, bs), 7.63 (4H, s), 9.89 (2H, bs).

Elemental analysis: Calcd. for C$_{17}$H$_{24}$N$_4$O$_2$: C, 64.53; H, 7.65; N, 17.71. Found: C, 64.51; H, 7.34; N, 17.59.

EXAMPLE 25

In the same manner as Example 1-(3) or 2-(3) or 3-(5), there are obtained the following compounds.

(1) 6-(4-Methoxyacetamidophenyl)-5-methyl-4,5-dihydro-1,2,4-triazin-3(2H)-one.

m.p. 225.5°-228° C. (recrystallized from 70% aqueous ethanol).

IR (Nujol) 3390, 3210, 3080, 1700 (shoulder), 1685 cm$^{-1}$.

NMR(DMSO-d$_6$, δ): 1.20(3H, d, J=7.2 Hz), 3.38(3H, s), 4.02(2H, s), 4.62 (1H, d, q, J=3, 7.2 Hz), 7.38 (1H, b.s.), 7.62(2H, d, J=8.2 Hz), 7.77(2H, d, J=8.2 Hz), 9.84(1H, b.s.), 9.91(1H, d, J=2 Hz).

(2) 6-(4-Isobutyrylaminophenyl)-5-methyl-4,5-dihydro-1,2,4-triazin-3(2H)-one.

m.p. 235°-239° C. (recrystallized from ethanol)

IR(Nujol) 3310, 3220, 3160, 3100, 3050, 1685 cm$^{-1}$.

NMR(DMSO-d$_6$, δ): 1.10(6H, d, J=6.4 Hz), 1.19(3H, d, J=6.8 Hz), Ca.2.4~2.8(1H, m), 4.60(1H, d, q, J=3.2, 6.8 Hz), 7.36(1H, b.s.), 7.64(4H, s), 9.90(2H, b.s.).

(3) 6-(4-Ethoxycarbonylaminophenyl)-5-methyl-4,5-dihydro-1,2,4-triazin-3(2H)-one.

m.p. 231°-235° C. (recrystallized from 80% aqueous ethanol).

NMR(DMSO-d$_6$, δ): 1.1~1.5(6H, complex), 4.15(2H, q, J=6 Hz), 4.60(1H, d, q, J=3.8, 6.2 Hz), Ca.7.4(1H, b.s.), 7.48(2H, d, J=10 Hz), 7.68(2H, d, J=10 Hz), 9.72(1H, s), 9.86(1H, b.s.).

(4) 6-(4-Phenylacetamidophenyl)-5-methyl-4,5-dihydro-1,2,4-triazin-3(2H)-one.

m.p. 204°-207° C. (recrystallized from aqueous ethanol)

IR(Nujol) 3250, 3100, 1710, 1660 cm$^{-1}$.

NMR(DMSO-d$_6$, δ): 1.21(3H, d, J=7 Hz), 3.68(2H, s), 4.61(1H, d, q, J=3.7 Hz), 7.31 (5H, s), Ca.7.4 (1H, b.s.), 7.65(4H, s), 9.91 (1H, b.s.), 10.25(1H, s).

(5) 6-(4-Acryloylaminophenyl)-5-methyl-4,5-dihydro-1,2,4-triazin-3(2H)-one.

NMR(DMSO-d$_6$, δ): 1.20(3H, d, J=7 Hz), 4.63(1H, d, q, J=3.7 Hz), 5.76 (1H, d, d, J=4.5, 8.5 Hz), 6.35 (1H, d, J=4.5 Hz), 6.39 (1H, d, J=8.5 Hz), 7.29~7.51(1H, m), 7.69(4H, s), 9.85~10.01(1H, m), 10.20~10.31(1H, m).

(6) 6-(4-Crotonoylaminophenyl)-5-methyl-4,5-dihydro-1,2,4-triazin-3(2H)-one.

m.p. 259°–263° C. (decomposition) (recrystallized from 70% aqueous ethanol).

IR(Nujol) 3220, 3080, 1680, 1585 cm$^{-1}$.

NMR(DMSO-d$_6$, δ): 1.21(3H, d, J=6.8 Hz), 1.88(3H, d, J=6.4 Hz), 4.64(1H, d, q, J=3.6, 6.8 Hz), 6.14(1H, b.d, J=15.2 Hz), 6.85(1H, d, q, J=15.2, 6.4 Hz), 7.39(1H, b.s.), 7.69(4H, s), 9.94(1H, b.s.), 10.05(1H, b.s.).

(7) 6-(3-Chloro-4-crotonoylaminophenyl)-5-methyl-4,5-dihydro-1,2,4-triazin-3(2H)-one.

m.p. 260°–264° C. (decomposition) (recrystallized from 70% aqueous ethanol).

IR(Nujol) 3400, 3200, 3080, 1700, 1690 cm$^{-1}$.

NMR(DMSO-d$_6$, δ): 1.21(3H, d, J=7 Hz), 1.88(3H, d, J=6.4 Hz), 4.65(1H, d, q, J=3.7 Hz), 6.31(1H, b.d., J=15 Hz), 6.87(1H, d, q, J=15, 6.4 Hz), 7.46(1H, b.s.), 7.63(1H, d, d, J=2, 8.4 Hz), 7.80(1H, d, J=2 Hz), 7.93(1H, d, J=8.4 Hz), 9.48(1H, b.s.), 10.05(1H, d, J=2 Hz).

(8) 6-[4-(4-Benzyloxyphenylacetamido)phenyl]-5-methyl-4,5-dihydro-1,2,4-triazin-3(2H)-one.

IR(Nujol) 3210, 1710, 1660 cm$^{-1}$.

NMR(DMSO-d$_6$, δ): 1.20(3H, d, J=6.2 Hz), 3.62(2H, s), 4.62(1H, m), 5.08 (2H, s), 6.96(2H, d, J=8.4 Hz), 7.1~7.9(12H, m), 9.92(1H, b.s.), 10.30(1H, b.s.).

(9) 6-(4-Cyclopropanecarbonylaminophenyl)-5-methyl-4,5-dihydro-1,2,4-triazin-3(2H)-one.

m.p. 288°–291° C. (recrystallized from aqueous dimethylformamide).

IR(Nujol) 3320, 3280, 3160, 3100, 1695, 1655 cm$^{-1}$.

NMR(DMSO-d$_6$, δ): 0.87(4H, broad d, J=5.2 Hz), 1.27(3H, d, J=6.6 Hz), 1.86(1H, broad quintet, J=6 Hz), 4.66(1H, d, q, J=3.4, 6.6 Hz), 7.41(1H, b.s.), 7.66(4H, s), 9.92(1H, b.s.), 10.28(1H, b.s.).

(10) 6-(4-Cyclobutanecarbonylaminophenyl)-5-methyl-4,5-dihydro-1,2,4-triazin-3(2H)-one.

m.p. 260°–262° C. (recrystallized from 70% aqueous ethanol).

IR(Nujol) 3300, 3200, 3090, 1686, 1672 cm$^{-1}$.

NMR(DMSO-d$_6$, δ): 1.17(3H, d, J=7 Hz), 1.5~2.5(6H, m), 3.20(1H, m), 4.62(1H, m), 7.37(1H, b.s.), 7.66(4H, s), 9.82(1H, b.s.), 9.91(1H, b.s.).

(11) 6-[4-(1-Adamantanecarbonylamino)phenyl]-5-methyl-4,5-dihydro-1,2,4-triazin-3(2H)-one.

m.p. >300° C. (recrystallized from aqueous dimethylformamide).

NMR(DMSO-d$_6$, δ): 1.19(3H, d, J=7 Hz), 1.71(6H, b.s.), 1.92(9H, b.s.), 4.61(1H, d, q, J=3,7 Hz), 7.36 (1H, b.s.), 7.68(4H, s), 9.19 (1H, s), 9.89(1H, b.s.).

(12) 6-(4-Mesylaminophenyl)-5-methyl-4,5-dihydro-1,2,4-triazin-3(2H)-one.

m.p. 261°–264° C. (recrystallized from 70% aqueous ethanol)

NMR(DMSO-d$_6$, δ): 1.22(3H, d, J=6.6 Hz), 3.04(3H, s), 4.61(1H, d, q, J=3.4, 6.6 Hz), 7.22(2H, d, J=9 Hz), 7.3(1H, b.s.), 7.70(2H, d, J=9 Hz), 9.90(2H, b.s.).

(13) 6-[4-(2,3-Dimethylpentanoylamino)phenyl]-5-methyl-4,5-dihydro-1,2,4-triazin-3(2H)-one.

m.p. 242°–244° C. (recrystallized from ethanol).

IR (Nujol) 3330, 3200, 3100, 1690, 1665 cm$^{-1}$.

NMR (DMSO-d$_6$, δ): 0.66–1.8 (12H, m), 1.19 (3H, d, J=7 Hz), 2.1–2.5 (1H, m), 4.59 (1H, d, q, J=3 Hz, 7 Hz), 7.36 (1H, bs), 7.63 (4H, s), 9.89 (2H, bs).

What is claimed is:

1. The compound, which is 6-(4-cyclopropanecarbonylaminophenyl)-5-methyl-4,5-dihydro-1,2,4-triazin-3(2H)-one.

2. The compound, which is 6-(4-cyclobutanecarbonylaminophenyl)-5-methyl-4,5-dihydro-1,2,4-triazin-3(2H)-one.

3. An antihypertensive, antithrombotic and antiulcer pharmaceutical composition comprising an effective amount of a compound of claim 1 or 2 for treating hypertension, thrombosis and ulcer.

4. A method for treating hypertension, thrombosis or ulcer which comprises administering a pharmaceutically effective amount of the antihypertensive, antithrombotic and antiulcer compound of claim 1 or 2.

5. The composition of claim 3 as an antihypertensive composition.

6. The composition of claim 3 as an antithrombotic composition.

7. The composition of claim 3 as an antiulcer composition.

8. The method of claim 4 for treating hypertension.

9. The method of claim 4 for treating thrombosis.

10. The method of claim 4 for treating ulcer.

11. The compound of claim 1 having antithrombotic activity.

12. The compound of claim 2 having antithrombotic activity.

* * * * *